US012605483B2

(12) United States Patent
Du et al.

(10) Patent No.: US 12,605,483 B2
(45) Date of Patent: Apr. 21, 2026

(54) PREPARATION METHOD FOR AND USE METHOD OF COLLAGEN MICROFIBER HEMOSTATIC MATERIAL

(71) Applicant: QUANFENG TECH (SHENZHEN) CO., LTD., Shenzhen (CN)

(72) Inventors: Mingchun Du, Chengdu (CN); Ci Qu, Beijing (CN)

(73) Assignee: QUANFENG TECH (SHENZHEN) CO., LTD., Shenzhen (CN)

( * ) Notice: Subject to any disclaimer, the term of this patent is extended or adjusted under 35 U.S.C. 154(b) by 549 days.

(21) Appl. No.: 18/098,512

(22) Filed: Jan. 18, 2023

(65) Prior Publication Data

US 2023/0173136 A1 Jun. 8, 2023

Related U.S. Application Data

(63) Continuation of application No. PCT/CN2021/132088, filed on Nov. 22, 2021.

(30) Foreign Application Priority Data

Nov. 23, 2020 (CN) .......................... 202011321222.5

(51) Int. Cl.
*A61L 26/00* (2006.01)

(52) U.S. Cl.
CPC ....... *A61L 26/0033* (2013.01); *A61L 26/0066* (2013.01); *A61L 26/0076* (2013.01); *A61L 2300/418* (2013.01)

(58) Field of Classification Search
CPC ............... A61L 24/102; A61L 2400/04; A61L 2300/418
See application file for complete search history.

(56) References Cited

U.S. PATENT DOCUMENTS

2007/0160543 A1 * 7/2007 Moller .................. A61K 38/45
128/200.23

FOREIGN PATENT DOCUMENTS

| | | | |
|---|---|---|---|
| CN | 107376000 A | 11/2017 | |
| CN | 107823693 A | 3/2018 | |
| CN | 107376000 B | * 8/2019 | .......... D01D 5/0015 |
| CN | 112516377 A | 3/2021 | |

OTHER PUBLICATIONS

CN-107376000-B (Google English translation, downloaded Jun. 2025) (Year: 2025).*
Liu et al (Advanced Biosystems, Mar. 2020, vol. 4, pp. 1-8) (Year: 2020).*
International search report of PCT/CN2021/132088, 5 pages.

* cited by examiner

*Primary Examiner* — Mark V Stevens
(74) *Attorney, Agent, or Firm* — Muncy, Geissler, Olds & Lowe, P.C.

(57) ABSTRACT

Disclosed in the present invention are a preparation method for and a use method of a collagen microfiber hemostatic material. Collagen microfibers are obtained by performing high-speed shearing on a solid collagen material; after the collagen microfibers are dispersed in an aqueous phase, a procoagulant active ingredient modifies the surfaces of the collagen microfibers by means of linking molecules; and a collagen microfiber hemostatic material is obtained by performing high-speed shearing again after freeze drying. The collagen microfiber material can be prepared simply and efficiently by means of high-speed shearing; the biological activity of the collagen material is maintained as much as possible; and the microfibers have a length range of 10-1000 μm and high dispersibility, thus facilitating spray processing. The procoagulant active ingredient can be efficiently and quantitatively loaded on the surfaces of the collagen microfibers by means of the linking molecules to enhance the hemostatic effect of the collagen microfibers. The collagen microfiber hemostatic material prepared in the present invention can be used for hemostasis of a bleeding wound by means of spraying application, thereby achieving the effect of non-contact fixed-point hemostasis.

8 Claims, 1 Drawing Sheet

PREPARATION METHOD FOR AND USE METHOD OF COLLAGEN MICROFIBER HEMOSTATIC MATERIAL

TECHNICAL FIELD

The present invention relates to a hemostatic material and a preparation method and a use method thereof, in particular to a preparation method for and a use method of a collagen microfiber hemostatic material.

BACKGROUND

As a clinically commonly used local hemostatic material, a solid collagen material has good hemostatic properties. By binding to platelets, the solid collagen material promotes aggregation of platelets and directly activates an endogenous coagulation pathway to produce a coagulation effect; meanwhile, blood cells adhere to form thrombus clots, thereby effectively preventing blood from washing away wounds. In addition, the collagen can promote formation of granulation tissues and accelerate healing of wounds. Moreover, the hemostatic activity of the collagen material is significantly superior to that of other polysaccharide hemostatic materials, and the collagen material can also have strong affinity with cells and growth factors in the wound healing process to promote wound repair and tissue regeneration. However, compared with some hemostatic materials (such as fibrinogen), there is still a gap in the hemostatic speed of the collagen materials. Therefore, shortening the hemostatic time has become one of the main research directions to improve the hemostatic performance of the collagen material.

SUMMARY OF THE INVENTION

In clinical applications, the shape of the hemostatic material also has a significant impact on its application. Hemostatic materials need to be able to adhere to the bleeding surface of complex organs for rapid hemostatic efficacy. Solid collagen materials are usually used for bleeding wounds in the form of collagen sheets, collagen membranes, collagen sponges, collagen fibers, collagen powder, etc. Among them, collagen fibers have the advantages of large specific surface area and easy adhesion.

For collagen fiber hemostatic materials, "CN109432489A" relates to a collagen hemostatic fiber cotton, and the collagen hemostatic fiber cotton is highly hydrophilic and can absorb blood or exudate within several seconds, quickly adhere to the wound surface, and promote platelet adhesion to form a thrombus, thereby realizing the effect of rapid and long-lasting hemostasis. However, due to a large size of the collagen fibers (up to centimeter level) in the collagen yarn, the collagen fibers eventually gather into clusters and are not dispersed, so they cannot be used for hemostasis of bleeding wounds by means of spraying.

For the collagen hemostatic powder material, "CN105597144A" relates to a collagen hemostatic powder, wherein collagen protein particles in a particle size range of 0.1-10 mm are prepared by spray drying the collagen solution. However, the temperature of spray drying is 100-130° C., and the collagen material treated at this temperature has been denatured, so the collagen material has a great impact on the biological activity and hemostatic efficacy of collagen.

In order to improve the hemostatic efficacy of collagen hemostatic materials (especially collagen fiber hemostatic materials), the present invention provides a collagen microfiber hemostatic material. The collagen microfiber can be prepared through high-speed shearing, and the size of the collagen microfiber can be controlled at a micron level, and the length of microfiber ranges from 10 μm-1000 μm with good dispersibility, i.e., with high dispersibility, and the collagen microfiber is more suitable for fast adhesion to bleeding wounds, and is also more convenient for spraying operation; high-speed shearing can ensure that the collagen material can be processed in a shorter time, and the collagen microfiber can be prepared efficiently and quickly, and the biological activity of the collagen material can be maintained as much as possible. The procoagulant active ingredients are loaded on the surface of the collagen microfiber through linking molecules to further increase the speed of hemostasis.

In the embodiment of the present invention, by means of spraying, the collagen microfiber hemostatic material of the present invention can act on the bleeding surface without contact and bind precisely to the bleeding point, therefore, the collagen microfiber hemostatic material is especially suitable for hemostasis of bleeding wounds in a narrow space such as brain surgery or liver surgery.

According to an aspect of the present invention, a preparation method of a collagen microfiber hemostatic material is provided, including the following steps:

(1) obtaining a collagen microfiber raw material by performing high-speed shearing on a solid collagen material;

(2) dispersing the collagen microfiber raw material (e.g., uniformly) obtained in step (1) in an aqueous phase with a mass ratio of the collagen fiber raw material to water ranging from 1:100 to 1:10,000 to configure a collagen microfiber suspension;

(3) filtering the collagen microfiber suspension obtained in step (2) through sieves of different meshes step by step to screen and obtain collagen microfibers in a length range of 10-1,000 μm, and dispersing in water to configure the collagen microfiber suspension;

(4) adding a procoagulant active ingredient to the collagen microfiber suspension obtained in step (3), with a mass ratio of the procoagulant active ingredient to the collagen microfiber ranging from 1:100 to 1:1,000,000;

(5) adding linking molecules to the collagen microfiber suspension obtained in step (4), wherein the linking molecule is one or a mixture of more than two of sulfonyl chloride, aldehyde, isothiocyanate, carbodiimide, acid anhydride, procyanidin, isocyanate, imide ester, genipin, acyl azide, and epoxide;

(6) performing freeze drying on the collagen microfiber suspension obtained in step (5) to obtain a collagen microfiber solid freeze-dried product; and (7) performing high-speed shearing on the collagen microfiber solid freeze-dried product obtained in step (6) through a high-speed pulverizer to obtain a highly dispersible collagen microfiber hemostatic material.

In the examples of the present invention, in step (1), a collagen microfiber raw material is obtained by performing high-speed shearing on a solid collagen material through a high-speed pulverizer, the solid collagen material is a collagen freeze-dried material, and the collagen freeze-dried material is selected from one or a combination of two or more of collagen membrane, collagen sheet, and collagen sponge.

In the examples of the present invention, the solid collagen material is cross-linked or not cross-linked.

In the examples of the present invention, the rotating speed of the high-speed pulverizer in both step (1) and step (7) is set to 20,000-60,000 r/min, and the pulverization time is set to 10 s-30 s.

In the preparation method of a collagen microfiber hemostatic material of the embodiment of the present invention, a solid collagen material of a large size (above the centimeter level) is rapidly cut through an instantaneous shearing force of a cutter head in a high-speed pulverizer to form a microfiber structure, and the extremely short pulverization time ensures that the temperature of the collagen material does not rise significantly, so that the collagen microfiber is prepared simply and efficiently without affecting the biological activity and other characteristics of the collagen material as much as possible. In order to avoid local temperature rise that may be caused by too much material and the like during the operation of the high-speed pulverizer, dry ice or liquid nitrogen can be added to the high-speed pulverizer for temperature reduction.

In the examples of the present invention, in step (2), the mass ratio of collagen fiber raw material to water ranges from 1:100 to 1:10,000, wherein the mass of the collagen fiber raw material is calculated according to the mass of the solid collagen material in step (1).

In the examples of the present invention, the mesh range of the sieve in step (3) is 16-1000 meshes.

In the examples of the present invention, in step (4), the procoagulant active ingredient is one or a combination of more than two of fibrinogen, prothrombin (thrombin), tissue factor (prothrombinase), calcium ion ($Ca^{2+}$), proaccelerin, thromboplastin, auxiliary thromboplastin, anti-hemophilic globulin A (AHG A), anti-hemophilic factor A (AHF A), platelet cofactor I, hemophilia factor VIII or A, anti-hemophilic globulin B (AHG B), anti-hemophilic factor B (AHF B), hemophilic factor IX or B, coagulation factor FX (STUART-PROWER-F), autologous prothrombin C, ROSENTHAL factor (hereditary coagulation factor), anti-hemophilic globulin C, HAGEMAN factor (Hagerman factor), and fibrous protein stabilizing factor.

In the examples of the present invention, in step (4), the mass ratio of the procoagulant active ingredient to the collagen microfiber ranges from 1:100 to 1:1,000,000, wherein the mass ratio of the procoagulant active ingredient to the collagen microfiber is the mass ratio of each ingredient in the procoagulant active ingredient to the solid collagen material in step (1).

In the examples of the present invention, in step (5), the imide ester includes NHS ester (N-hydroxysuccinimide ester).

In the examples of the present invention, in step (5), the final concentration of the linking molecules in the collagen microfiber suspension is greater than or equal to 0.001 wt. % but less than or equal to 1 wt. %. In an example, the final concentration of each ingredient in the linking molecules in the collagen microfiber suspension is greater than or equal to 0.001 wt. % but less than or equal to 1 wt. %.

In the examples of the present invention, in step (5), the reaction time of the linking molecules in the collagen microfiber suspension is 30 min-120 min (minutes); preferably, the reaction time of the linking molecules in the collagen microfiber suspension is 30 min-60 min.

In the examples of the present invention, in steps (4) and (5), the procoagulant active ingredient is loaded on the surface of the collagen microfiber by means of linking molecules. The reaction is mild and does not affect the biological activity and hemostatic efficacy of the collagen material and the procoagulant active ingredient. Moreover, since too little loading of the procoagulant active ingredient does not significantly enhance the hemostatic effect of the collagen microfiber material, or too much loading of the procoagulant active ingredient may cause intravascular thrombosis, etc., the amount of the procoagulant active ingredient and linking molecules needs to be regulated in order to achieve the desired hemostatic effect.

In the examples of the present invention, in step (6), the collagen microfibers in the collagen microfiber freeze-dried material will agglomerate due to freeze-dried processing, and the dispersibility of the collagen microfibers will become poor and unfavorable for spray processing, so in step (7), the collagen microfibers with high dispersibility are prepared again by shearing and dispersing the agglomerated collagen microfibers again through a high-speed pulverizer. The collagen microfiber hemostatic material thus produced can be applied to the bleeding wound by spraying.

According to another aspect of the present invention, a use method of a collagen microfiber hemostatic material is provided, and the collagen microfiber hemostatic material is prepared according to the preparation method for the collagen microfiber hemostatic material described in any of the preceding examples.

In the examples of the present invention, the collagen microfiber hemostatic material is sprayed by a spraying device for hemostasis, for example, on a bleeding wound, wherein a nozzle in the spraying device has an inner diameter of 2 mm-5 mm. The inner diameter size of the nozzle matches the length range of the collagen microfiber of the present invention, thereby ensuring that the collagen microfiber hemostatic material can be sprayed smoothly through the spraying device without blocking the nozzle.

In the examples of the present invention, the collagen microfiber hemostatic material is applied to hemostasis of bleeding wounds in brain surgery or liver surgery.

Compared with conventional collagen hemostatic materials, the collagen microfiber hemostatic material of the present invention has at least one of the following advantages: 1. the collagen microfiber has the characteristics of micron-sized size and high dispersibility, and is suitable for contactless application of the collagen microfibers to the bleeding surface by spraying, especially for narrow and high-risk bleeding wounds, such as bleeding in brain surgery; 2. the micron-sized collagen fibers are more suitable for rapid adhesion to bleeding wounds and precise binding to the bleeding point, so an effect of localized hemostasis can be achieved; 3. the high-speed shearing method allows for efficient and rapid preparation of collagen microfibers, thereby maintaining the biological activity of the collagen material as much as possible; and 4. the linking molecules can efficiently load procoagulant active ingredients on the surface of collagen microfibers, with faster hemostatic speed and better hemostatic effect.

DETAILED DESCRIPTION

Figures 1A, 1B:
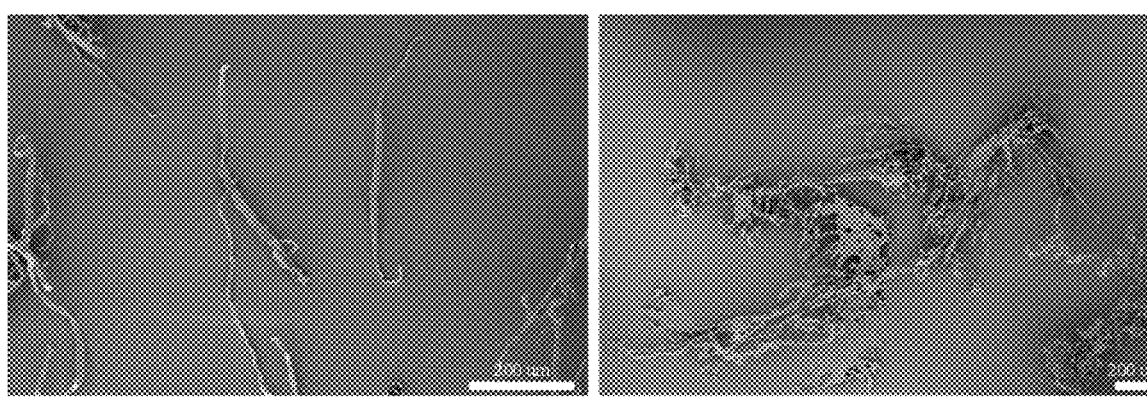
FIGS. 1A-1B show a comparison of the size and dispersibility of the collagen microfiber hemostatic material (FIG. 1A is a sample made according to the preparation method of Example 1 of the present invention, and FIG. 1B is a sample of Contrast Example 1)

The technical solutions of the present invention are further specified below by means of embodiments and in combination with the accompanying drawings. Throughout the specification, identical or similar appended symbols indicate identical or similar components.

The following description of embodiments of the present invention with reference to the accompanying drawings is intended to explain the general inventive concept of the present invention and should not be understood as a limitation of the present invention.

Example 1

A preparation method for a collagen microfiber hemostatic material is provided, wherein the following steps are included in sequence:

(1) shearing 5 g of cross-linked collagen sheets at a high speed on a high-speed pulverizer and obtaining the collagen microfiber raw material, wherein the rotating speed of the high-speed pulverizer is 30,000 r/min and the pulverization time is 30 s;

(2) uniformly dispersing the collagen microfiber raw material obtained in step (1) in 500 g of deionized water to configure a collagen microfiber suspension;

(3) filtering the collagen microfiber suspension obtained in step (2) through sieves of 30-150 meshes step by step, screening to obtain a collagen microfiber raw material in a length range of 100-500 μm, and dispersing in water to configure the collagen microfiber suspension;

(4) adding 50 mg of fibrinogen and 2 mg of calcium chloride to the collagen microfiber suspension obtained in step (3);

(5) adding 5 mg of glutaraldehyde and 10 mg of NHS ester to the collagen microfiber suspension obtained in step (4) for a reaction time of 30 min;

(6) performing freeze drying on the collagen microfiber suspension obtained in step (5) to obtain a collagen microfiber solid freeze-dried product; and (7) performing high-speed shearing on the collagen microfiber solid freeze-dried product obtained in step (6) through a high-speed pulverizer, wherein the rotating speed of the high-speed pulverizer is 40,000 r/min and the pulverization time is 10 s, to obtain the collagen microfiber hemostatic material.

The above collagen microfiber hemostatic material was sprayed onto the bleeding wound in craniotomy for hemostasis treatment by a spraying device with a nozzle inner diameter of 3 mm.

Example 2

A preparation method for a collagen microfiber hemostatic material is provided, wherein the following steps are included in sequence:

(1) shearing 10 g of collagen membranes at a high speed on a high-speed pulverizer and obtaining the collagen microfiber raw material, wherein the rotating speed of the high-speed pulverizer is 20,000 r/min and the pulverization time is 20 s;

(2) uniformly dispersing the collagen microfiber raw material obtained in step (1) in 100,000 g of deionized water to prepare a collagen microfiber suspension;

(3) filtering the collagen microfiber suspension obtained in step (2) through sieves of 16-40 meshes step by step, screening to obtain a collagen microfiber raw material in a length range of 400-1,000 μm, and dispersing in water to configure the collagen microfiber suspension;

(4) adding 0.5 mg of proaccelerin and 0.01 mg of platelet cofactor I to the collagen microfiber suspension obtained in step (3);

(5) adding 2 g of ethylene oxide and 1 g of procyanidin to the collagen microfiber suspension obtained in step (4) for a reaction time of 60 min;

(6) performing freeze drying on the collagen microfiber suspension obtained in step (5); and (7) performing high-speed shearing on the collagen microfiber solid freeze-dried product obtained in step (6) through a high-speed pulverizer, wherein the rotating speed of the high-speed pulverizer is 30,000 r/min and the pulverization time is 20 s, to obtain the collagen microfiber hemostatic material.

The above collagen microfiber hemostatic material was sprayed onto the bleeding wound in liver surgery for hemostasis treatment by a spraying device with a nozzle inner diameter of 5 mm.

Example 3

A preparation method for a collagen microfiber hemostatic material is provided, wherein the following steps are included in sequence:

(1) shearing 2 g of collagen sponge at a high speed on a high-speed pulverizer and obtaining the collagen microfiber raw material, wherein the rotating speed of the high-speed pulverizer is 60,000 r/min and the pulverization time is 10 s;

(2) uniformly dispersing the collagen microfiber raw material obtained in step (1) in 500 g of deionized water to prepare a collagen microfiber suspension;

(3) filtering the collagen microfiber suspension obtained in step (2) through sieves of 80-1,000 meshes step by step, screening to obtain a collagen microfiber raw material in a length range of 10-200 μm, and dispersing in water to configure the collagen microfiber suspension;

(4) adding 1 mg of thrombinogenase to the collagen microfiber suspension obtained in step (3);

(5) adding 0.02 g of carbodiimide and 5 g of genipin to the collagen microfiber suspension obtained in step (4) for a reaction time of 120 min;

(6) performing freeze drying on the collagen microfiber suspension obtained in step (5); and (7) performing high-speed shearing on the collagen microfiber solid freeze-dried product obtained in step (6) through a high-speed pulverizer, wherein the rotating speed of the high-speed pulverizer is 50,000 r/min and the pulverization time is 10 s, to obtain the collagen microfiber hemostatic material.

The above collagen microfiber hemostatic material was sprayed onto the bleeding skin wound for hemostasis treatment by a spraying device with a nozzle inner diameter of 2 mm.

Comparative Test of Effects of Collagen Microfiber
Hemostatic Materials

I. Contrast of the Preparation of Collagen
Hemostatic Materials

Contrast Example 1: A Preparation Method for a
Collagen Fiber Hemostatic Material is Provided,
Wherein the Following Steps are Included in
Sequence uniformly dispersing 2 g of collagen sponge in 500 g of deionized water, to obtain a collagen fiber hemostatic material by means of freeze drying; and covering the above collagen fiber hemostatic material on the bleeding skin wound for hemostasis treatment.

Contrast Example 2: A Preparation Method for a
Collagen Microfiber Hemostatic Material is
Provided, Wherein the Following Steps are
Included in Sequence (1) shearing 10 g of collagen membranes at a high speed on a high-speed pulverizer and obtaining the collagen microfiber raw material, wherein the rotating speed of the high-speed pulverizer is 20,000 r/min and the pulverization time is 20 s;

(2) uniformly dispersing the collagen microfiber raw material obtained in step (1) in 10,000 g of deionized water to configure a collagen microfiber suspension;

(3) filtering the collagen microfiber suspension obtained in step (2) through sieves of 16-40 meshes step by step, screening to obtain a collagen microfiber raw material in a length range of 400-1,000 μm, and dispersing in water to configure the collagen microfiber suspension;

(4) performing freeze drying on the collagen microfiber suspension obtained in step (3); (5) performing high-speed shearing on the collagen microfiber solid freeze-dried product obtained in step (4) through a high-speed pulverizer, wherein the rotating speed of the high-speed pulverizer is 30,000 r/min and the pulverization time is 10 s, to obtain the collagen microfiber hemostatic material.

The above collagen microfiber hemostatic material was sprayed onto the bleeding wound in liver surgery for hemostasis treatment by a spraying device with a nozzle inner diameter of 5 mm.

Contrast Example 3: A Preparation Method for a
Collagen Microfiber Hemostatic Material is
Provided, Wherein the Following Steps are
Included in Sequence (1) shearing 5 g of cross-linked collagen sheets at a high speed on a high-speed pulverizer and obtaining the collagen microfiber raw material, wherein the rotating speed of the high-speed pulverizer is 30,000 r/min and the pulverization time is 30 s;

(2) uniformly dispersing the collagen microfiber raw material obtained in step (1) in 500 g of deionized water to configure a collagen microfiber suspension;

(3) filtering the collagen microfiber suspension obtained in step (2) through sieves of 30-150 meshes step by step, screening to obtain a collagen microfiber raw material in a length range of 100-500 μm, and dispersing in water to configure the collagen microfiber suspension;

(4) adding 50 mg of fibrinogen and 2 mg of calcium chloride to the collagen microfiber suspension obtained in step (3);

(5) performing freeze drying on the collagen microfiber suspension obtained in step (4); and (6) performing high-speed shearing on the collagen microfiber solid freeze-dried product obtained in step (5) through a high-speed pulverizer, wherein the rotating speed of the high-speed pulverizer is 40,000 r/min and the pulverization time is 10 s, to obtain the collagen microfiber hemostatic material.

The above collagen microfiber hemostatic material was sprayed onto the bleeding wound in craniotomy for hemostasis treatment by a spraying device with a nozzle inner diameter of 3 mm.

Contrast Example 4: A Preparation Method for
Collagen Hemostatic Powder is Provided, Wherein
the Following Steps are Included in Sequence (1) placing 1 g of type I collagen material into 1000 g of deionized water, and adding 0.1 M of acetic acid solution to dissolve the collagen in the stirring process to form a homogeneous solution; and (2) preparing the collagen solution in step (1) by a spray dryer into collagen protein particles with a particle size range of 0.2-1 mm at a temperature of 110° C.

The above collagen hemostatic powder was sprayed onto the bleeding wound in liver surgery by a spraying device with a nozzle inner diameter of 5 mm.

II. Contrast of Effect Tests (1) Contrast test of collagen fiber size and dispersibility: the collagen fiber samples in Example 1 and Contrast Example 1 were dehydrated in a gradient manner in high-concentration ethanol solution (25, 50, 70, 80, 90, 95, 100% (v/v %) for 1 hour (h) per immersion. The sample surface was processed with platinum spray (Pt) and observed on a scanning electron microscope (SEM) (S-4800, Hitachi) with an accelerating voltage of 15 kV. The results are shown in FIG. 1. The collagen microfibers in Example 1 are obtained through high-speed shearing, and as can be seen from FIG. 1A, the collagen microfibers in Example 1 can be of a micron size and are well dispersed for spray processing. The collagen fibers in Contrast Example 1 are obtained through conventional freeze drying, and as can be seen from FIG. 1B, the collagen fibers in Contrast Example 1 are at a centimeter level in size, and the fibers are intertwined with each other with poor dispersibility, which is not favorable for spray processing. This can confirm that highly dispersible collagen microfiber material can be prepared rapidly and efficiently through high-speed shearing, and that the highly dispersible collagen microfiber material is more suitable for spray processing and can act on the bleeding wound without contact.

Figures 2A, 2B:
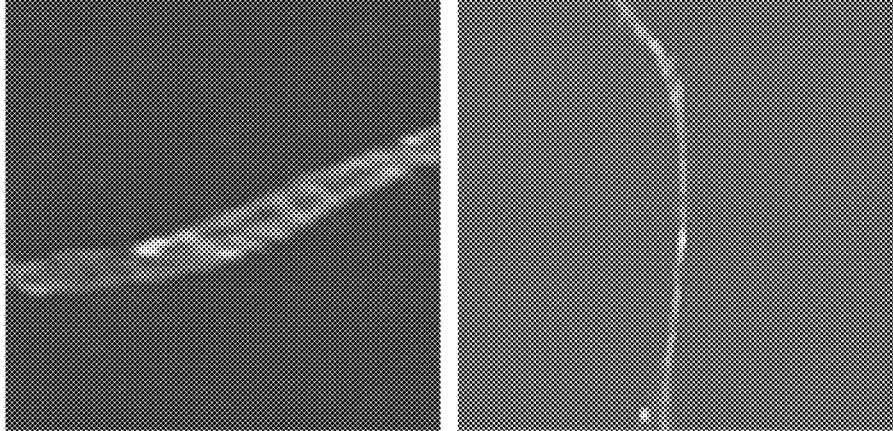
FIGS. 2A-2D show a comparison of the loading of the collagen microfiber hemostatic material with the procoagulant active ingredient (FIG. 2A is a sample made according to the preparation method of Example 2 of the present invention, FIG. 2B is a sample made according to the preparation method of Example 3 of the present invention, FIG. 2C is a sample of Contrast Example 2, and FIG. 2D is a sample of Contrast Example 3).
Figures 2C, 2D:
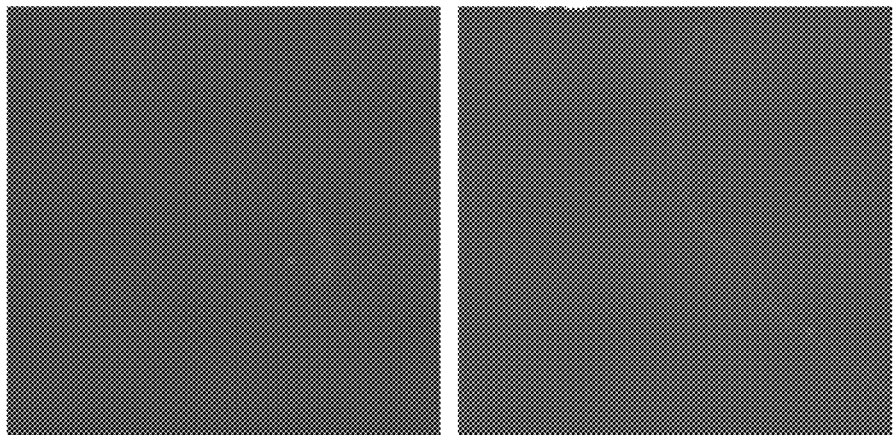

(2) Contrast test of collagen microfiber loaded with procoagulant active ingredients: after the procoagulant active ingredients in Examples 2-3 as well as in Contrast Example 3 were labeled with fluorescein isothiocyanate (FITC) fluorescent dye, corresponding collagen microfiber materials were prepared respectively; the collagen microfiber materials were observed on an A1 laser confocal microscope (Nikon) using a green excitation light wavelength of 488 nm, and the loading of procoagulant active ingredients on collagen microfibers was compared, and the results can be seen in FIG. 2. It can be seen in FIG. 2 that the linking molecules in the collagen microfiber hemostatic material in the examples can promote the loading of the procoagulant active ingredient on the collagen microfiber, and the procoagulant active ingredient is labeled with the green fluorescent dye FITC, so a strong fluorescent signal (e.g., a green fluorescent signal) can be observed, thereby indicating that the collagen microfibers in Examples 2-3 are loaded with a large number of procoagulant active ingredients (see FIG. 2A and FIG. 2B); no procoagulant active ingredient and linking molecule is added in Contrast Example 2, and no fluorescent signal (e.g., a green fluorescence signal) can be observed, thereby indicating that the collagen microfiber in Contrast Example 2 is not loaded with the procoagulant active ingredient (see FIG. 2C); the procoagulant active ingredient is added in Contrast Example 3 but no linking molecule is added, and the procoagulant active ingredient is not easily loaded on the surface of the collagen microfiber, so only a weak fluorescent signal (e.g., a green fluorescent signal) can be observed, thereby indicating that the collagen microfiber in Contrast Example 3 is loaded with an extremely small number of procoagulant active ingredients (see FIG. 2D). This confirms that the procoagulant active ingredient can be efficiently loaded on the surface of the collagen microfiber by means of linking molecules.

(3) Contrast test of the hemostatic effect of collagen hemostatic material in a rat hemorrhagic wound model: 70 SD rats, weighing 275-300 g, were adopted and housed at a controlled temperature of 20-25° C., with adequate light and free diet and water. All experimental animal procedures were in accordance with the "Guideline for the Management and Use of Laboratory Animals". A random number table method was used to divide the rats into 1-3 groups in the Example and 1-4 groups in the Contrast Example, with 10 rats in each group. Data were statistically analyzed by Statistical Products and Services Solutions Software (SPSS), wherein $p < 0.05$ was considered a significant difference in data. The collagen hemostatic materials in Examples 1-3 and Contrast Examples 1-4 are applied to the corresponding bleeding wounds for hemostasis using the corresponding methods, and the hemostatic time is the time used from the application of the material on the bleeding wounds to the absence of blood exudation from the bleeding wounds, and the hemostatic time of different samples is shown in Table 1.

efficiency of the procoagulant ingredients on the surface of the collagen microfiber is not high due to a lack of linking molecules, and the hemostatic speed cannot be improved dramatically; although the collagen hemostatic powder in Contrast Example 4 is micron-sized particles, the biological activity of the collagen material is affected by high temperature processing during the preparation process, the hemostatic efficacy is weakened, and the hemostatic time is also longer than the hemostatic time of the sample in the examples.

It can be seen in combination with the effect tests that, compared with the collagen hemostatic material in the contrast example, the collagen microfiber hemostatic material in the examples has the characteristics of micron size and high dispersibility, and is suitable for applying the collagen microfiber to the bleeding surface without contact by spraying, especially suitable for narrow and high-risk bleeding wounds; the collagen microfiber hemostatic material in the examples is more suitable for quickly adhering to bleeding wounds and precisely combining with bleeding points, and the effect of positioned bleeding can be achieved; the collagen microfiber hemostatic material in the examples is prepared efficiently and rapidly by a high-speed shearing method, thereby maintaining its biological activity as much as possible; for the collagen microfiber hemostatic material in the examples, the linking molecules can be efficiently loaded with procoagulant active ingredients on the surface of the collagen microfiber, thereby resulting in faster hemostatic speed and better hemostatic effect.

The above described examples are merely a description of the preferred embodiments of the present invention, and under a premise of not departing from the design spirit of the present invention, various deformations and improvements made to the technical solutions of the present invention by those skilled in the art shall all fall within the protection scope determined by the claims of the present invention.

The invention claimed is:

1. A preparation method of a collagen microfiber hemostatic material, comprising the following steps:
    (1) obtaining a collagen microfiber raw material by performing shearing on a solid collagen material;
    (2) dispersing the collagen microfiber raw material obtained in step (1) in an aqueous phase with a mass

TABLE 1

| | Comparison of hemostatic time of collagen hemostatic material in rat bleeding wound model | | | | | | |
|---|---|---|---|---|---|---|---|
| | Example 1 | Example 2 | Example 3 | Contrast Example 1 | Contrast Example 2 | Contrast Example 3 | Contrast Example 4 |
| Hemostatic time (s) | 11.3 ± 0.5 | 16.8 ± 0.2 | 18.2 ± 0.3 | 75.7 ± 0.6 | 67.3 ± 0.8 | 53.6 ± 0.7 | 65.3 ± 0.8 |

As can be seen from Table 1, the effect of hemostasis can be achieved basically within 20 s since the collagen microfiber hemostatic materials in the examples can rapidly adhere to the bleeding wounds and since procoagulant active ingredients are efficiently loaded on the surface of the materials; while the hemostatic time of the collagen fiber materials in Contrast Examples 1-3 is above 50 s, especially in Contrast Examples 1 and 2 in which no procoagulant active ingredient is added, the hemostatic time is above 60 s, which is significantly greater than the hemostatic time of the sample in the examples; although procoagulant active ingredients are added in Contrast Example 3, the loading ratio of the collagen fiber raw material to water ranging from 1:100 to 1:10,000 to configure a collagen microfiber suspension;
    (3) filtering the collagen microfiber suspension obtained in step (2) through sieves of different meshes to screen and obtain collagen microfibers in a length range of 10-1,000 μm, and dispersing in water to configure the collagen microfiber suspension;
    (4) adding a procoagulant active ingredient to the collagen microfiber suspension obtained in step (3), with a mass ratio of the procoagulant active ingredient to the collagen microfibers ranging from 1:100 to 1:1,000,000;

(5) adding linking molecules to the collagen microfiber suspension obtained in step (4), wherein the linking molecule is one or a mixture of more than two of sulfonyl chloride, aldehyde, isothiocyanate, carbodiimide, acid anhydride, procyanidin, isocyanate, imide ester, genipin, acyl azide, or epoxide, wherein the final concentration of the linking molecules in the collagen microfiber suspension is greater than or equal to 0.001 wt. % but less than or equal to 1 wt. %, and wherein a time of the linking molecules in the collagen microfiber suspension is 30 min-120 min;

(6) performing freeze drying on the collagen microfiber suspension obtained in step (5) to obtain a collagen microfiber solid freeze-dried product; and (7) performing shearing on the collagen microfiber solid freeze-dried product obtained in step (6) through a pulverizer to obtain a dispersible collagen microfiber hemostatic material.

2. The preparation method for a collagen microfiber hemostatic material of claim 1, wherein in step (1), a collagen microfiber raw material is obtained by performing shearing on a solid collagen material through a pulverizer, the solid collagen material is a collagen freeze-dried material, and the collagen freeze-dried material is selected from one or a combination of more than two of collagen membrane, collagen sheet, or collagen sponge.

3. The preparation method of a collagen microfiber hemostatic material of claim 1, wherein the solid collagen material is cross-linked.

4. The preparation method of a collagen microfiber hemostatic material of claim 2, wherein the rotating speed of the pulverizer in both step (1) and step (7) is set to 20,000-60,000 r/min, and the pulverization time is set to 10 s-30 s.

5. The preparation method of a collagen microfiber hemostatic material of claim 1, wherein in step (4), the procoagulant active ingredient is one or a combination of more than two of fibrinogen, prothrombin, tissue factor, calcium ion, proaccelerin, thromboplastin, auxiliary thromboplastin, anti-hemophilic globulin A, platelet cofactor I, anti-hemophilic globulin B, coagulation factor X, autoprothrombin C, Rosenthal factor, anti-hemophilic globulin C, Hageman factor, or fibrin stabilizing factor.

6. The preparation method of a collagen microfiber hemostatic material of claim 1, wherein the imidate ester in step (5) is an N-hydroxysuccinimide ester.

7. A method of using the collagen microfiber hemostatic material of claim 1, comprising preparing the collagen microfiber hemostatic material according to the preparation method of the collagen microfiber hemostatic material.

8. The method of using the collagen microfiber hemostatic material of claim 7, comprising spraying the collagen microfiber hemostatic material by a spraying device, wherein a nozzle in the spraying device has an inner diameter of 2 mm-5 mm.

* * * * *